United States Patent [19]

Krespan

[11] Patent Number: 4,686,300

[45] Date of Patent: Aug. 11, 1987

[54] POLYFLUORO GAMMA-KETOESTERS AND 5-HYDROXY GAMMA LACTONE ANALOGUES THEREOF

[75] Inventor: Carl G. Krespan, Wilmington, Del.

[73] Assignee: E. I. Du Pont de Nemours and Company, Wilmington, Del.

[21] Appl. No.: 472,985

[22] Filed: Mar. 7, 1983

[51] Int. Cl.[4] .................. C07C 149/16; C07D 307/32
[52] U.S. Cl. .................... 549/313; 548/546; 549/324
[58] Field of Search .............. 560/174; 549/313, 324

[56] References Cited

U.S. PATENT DOCUMENTS

| | | | |
|---|---|---|---|
| 2,493,676 | 1/1950 | Langlois et al. | 549/313 |
| 2,802,028 | 8/1957 | England | 260/539 |
| 2,988,537 | 6/1961 | Wiley | 260/67 |
| 3,274,239 | 9/1966 | Selman | 260/514 |
| 3,847,978 | 11/1974 | Sianese et al. | 260/535 H |
| 3,954,807 | 5/1976 | Erby et al. | 549/324 |
| 4,131,740 | 12/1978 | England | 560/180 |
| 4,273,728 | 6/1981 | Krespan | 260/465.6 |
| 4,273,729 | 6/1981 | Krespan | 260/543 F |
| 4,275,225 | 6/1981 | Krespan | 560/174 |
| 4,275,226 | 6/1981 | Yamabe et al. | 560/183 |
| 4,330,654 | 5/1983 | Ezzell et al. | 526/243 |
| 4,335,255 | 6/1982 | Krespan | 560/174 |
| 4,337,211 | 6/1982 | Ezzell et al. | 260/456 F |

FOREIGN PATENT DOCUMENTS

| | | |
|---|---|---|
| 41736 | 12/1981 | European Pat. Off. |
| 41737 | 12/1981 | European Pat. Off. |
| 41735 | 12/1981 | European Pat. Off. |
| 2051831 | 1/1981 | United Kingdom |

OTHER PUBLICATIONS

McBee et al., J. Am. Chem. Soc. 75: 3152-3153 (1953).

*Primary Examiner*—Glennon H. Hollrah
*Assistant Examiner*—D. B. Springer

[57] ABSTRACT

Polyfluoro γ-ketoester compounds are obtained by reaction of ethylenic monoolefins, a metal or quaternary ammonium cyanide, and a fluoroester. These compounds, which have a general formula $R_FC(O)CFYCF_2CO_2R^1$, can be copolymerized directly with fluorinated ethylenic monoolefins, or further reacted to form vinyl ether and allyl ether derivatives which may also be copolymerized with ethylenic comonomers, forming solid, moldable copolymers with useful properties determined by the nature of pendant functional groups $R_F$.

5 Claims, No Drawings

POLYFLUORO GAMMA-KETOESTERS AND 5-HYDROXY GAMMA LACTONE ANALOGUES THEREOF

BACKGROUND OF THE INVENTION

This invention relates to certain polyfluoro γ-ketoester compounds and derivatives, to processes for their preparation, and to certain copolymers prepared therefrom.

Wiley, U.S. Pat. No. 2,988,537, discloses a synthesis of certain β-alkoxypolyfluoroketones according to the following sequence:

$$MOR^1 + CX_2=CX_2 + R^2CO_2R^3 \longrightarrow$$

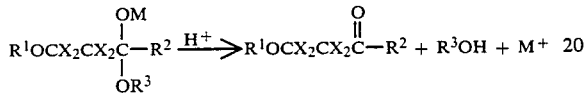

wherein X is halogen, M is an alkali metal and $R^1$ and $R^3$ are alkyl or polyfluorinated alkyl groups having up to 18 carbon atoms. $R^2$ may be hydrogen, an alkyl group or polyfluorinated alkyl group having up to 12 carbon atoms, or an aromatic or arylaliphatic group.

England, U.S. Pat. No. 2,802,028, discloses a process for preparing polyfluoroamides and polyfluorocarboxylic acids of the formula $HCXYCF_2CO_2M$. According to this process, an addition reaction of an alkali metal cyanide and water with fluoroolefins of formula $CF_2=CXY$, followed by hydrolysis, yields the carboxylic acid and amide. In the foregoing formula, X is —F or —Cl, Y is —F, —H, —Cl, an alkyl, cycloalkyl, fluoro- or chloro-substituted alkyl group, and M is an alkali metal.

Selman, U.S. Pat. No. 3,274,239, discloses a process for preparing acyl fluorides of the formula

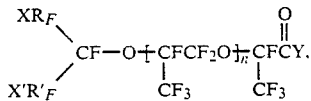

by reacting hexafluoropropene oxide (HFPO) with fluoroketones of formula $XR_FC(O)R'_FX'$, wherein $R_F$ and $R'_F$ are $C_{1-8}$ perfluoroalkylene groups, X and X' are hydrogen or halogen, Y is hydroxyl or fluorine, and n is an integer from zero to twenty. Selman also discloses a process for preparation of vinyl ether derivatives by pyrolysis of the corresponding acyl fluoride compounds.

Krespan, U.S. Pat. No. 4,335,255, discloses fluoroketoesters of the formula

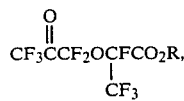

wherein R is a $C_{1-8}$ alkyl group. In addition to a process for preparing the fluoroketoesters, the patent further discloses the reaction of the fluoroketoesters with HFPO to form HFPO adduct acyl fluorides of the formula

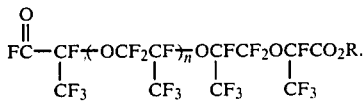

Pyrolysis of the acyl fluorides in the presence of alkali metal basis salts yields vinyl ethers of formula

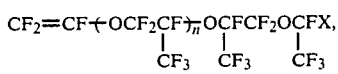

where X can be selected from $CO_2M$, $CO_2R$, $CO_2H$, COF, COCl, $CONH_2$ or CN, M is alkali metal, and n is 0 to 6. This patent also describes reaction of the acyl fluorides with perfluoroallyl fluorosulfate, perfluoroallyl fluorochloride or -bromide to yield perfluoroallyl derivatives of the formula

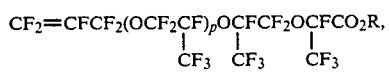

where p is 0 to 7, inclusive. Finally, copolymerization of the perfluorovinyl ether and perfluoroallyl ether derivatives with fluorinated vinyl monomers such as tetrafluoroethylene, trifluoroethylene, chlorotrifluoroethylene, or vinylidene fluoride is disclosed.

Sianesi, et al., U.S. Pat. No. 3,847,978, disclose fluoroketoesters of the formula $$CF_3C(O)CF_2[CF(CF_3)CF_2O]_mCF(CF_3)CO_2R,$$

and certain copolymers derived therefrom, where R is —H or an alkyl group, and m is an integer between 1 and 50, inclusive.

England, U.S. Pat. No. 4,131,740, discloses α-carboxylate-ω-vinyl ethers of the formula

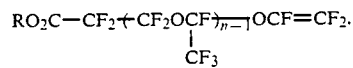

wherein R is a $C_{1-6}$ alkyl group, and n is 1-6. Processes for preparing these compounds by pyrolysis of the corresponding acyl fluorides in the presence of $Na_2CO_3$ or $Na_3PO_4$, and copolymers of the vinyl ethers and such perfluorinated vinyl monomers as tetrafluoroethylene are also described.

McBee, et al., *J. Am. Chem. Soc.* 75: 3152–3153, disclose a process for synthesizing polyfluoro β-ketoester compounds of formula

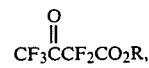

by a Claisen condensation of polyfluorinated acetate esters using NaH as a condensing agent. R in the foregoing formula can be —H or —$C_2H_5$.

Kimoto el al., British Patent Application No. 2,051,831 A, disclose substituted fluorocarbons of formula $X(CF_2)_nY$, wherein X includes —SR and —$SO_2R$ substituents and Y can be an acyl halide or vinyl ether substituent, for example:

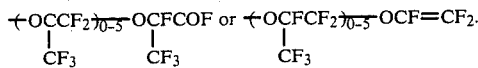

This reference also discloses copolymers of the vinyl ether derivatives and fluorinated olefins, and preparation of ion-exchange membranes from these copolymers which are suitable for use in chlor-alkali electrolysis cells.

Yamabe, et al., U.S. Pat. No. 4,275,226, describe a process for preparing fluorovinyl ether compounds of the formula $XR_FCF_2OCF=CF_2$, wherein X is —H, —Cl, —Br, —F, —CONRR', —COF, —CO$_2$R, —SO$_2$F or —PO(OR)$_2$, R is a C$_{1-10}$ alkyl group, R' is —H or a C$_{1-10}$ alkyl group, and $R_F$ is a C$_{1-20}$ bifunctional perfluoro-containing group optionally containing one or more ether bonds. According to this process, an iodine-containing polyfluorinated ether compound of formula $XR_FCF_2OCF_2CF_2I$ is reacted with a metallic catalyst to form a fluoro-organometallic compound which is subsequently heated to form the vinyl ether.

Ezzell, et al., U.S. Pat. No. 4,337,211 and European Patent Application (E.P.A.) 41,736, disclose compounds having the formula

wherein Y can be —SO$_2$Z, —C(O)Z, or —P(O)Z$_2$; Z can be —OH, —OA, —F, —Br or —Cl; A is alkali metal, quaternary ammonium or R; R is alkyl or aryl; a and b are 0 or an integer, and $R_F$ and $R'_F$ are each —F, —Cl, perfluoroalkyl or perfluorochloroalkyl. This reference further discloses an ether derivative of the formula

wherein X is —F, —Cl, or —Br, or mixtures thereof when n is greater than 1; X' is —Cl or —Br, or mixtures thereof when m is greater than 1; a and b are 0 or an integer, and m and n are 0 or an integer.

Ezzell, et al., U.S. Pat. No. 4,330,654 and E.P.A. 41,737 and 41,735, disclose vinyl ethers prepared from the aforementioned ether derivative of U.S. Pat. No. 4,337,211 which have the formula

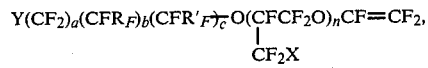

as well as certain copolymers derived by reaction of the vinyl ether derivatives with fluorinated olefins.

Finally, Krespan, U.S. Pat. Nos. 4,273,728, 4,273,729 and 4,275,225 each disclose polyfluoroallyl ethers $CF_2=CFCF_2OR_F$, wherein $R_F$ includes the group $[CF_2CF(CF_3)O]_nR^3Q$, where $R^3$ is a linear or branched perfluoroalkylene group and Q is a functional group including —CO$_2$R, where R is a methyl or ethyl group. Fluorinated copolymers of these allyl ether compounds and fluorovinyl monomers are also disclosed.

SUMMARY OF THE INVENTION

In accordance with the present invention, there is provided a polyfluoro γ-ketoester compound of the formula:

wherein $R_F$ is —CF$_3$ or —$R^1_FX$, where $R^1_F$ is a C$_{2-10}$ perfluoroalkylene group optionally containing 1 or 2 in-chain ether oxygen atoms separated by at least two carbon atoms, and X is —F, —OR$^2$, —SR$^2$, —SO$_2$R$^2$, —SO$_2$F, —SO$_2$Cl or —N$_3$, where R$^2$ is —CH$_3$, —C$_2$H$_5$ or —C$_6$H$_5$, R$^1$ is —CH$_3$, —C$_2$H$_5$, —CH$_2$CF$_3$ or —CH$_2$(CF$_2$CF$_2$)$_{1-6}$H, and Y is —F or —Cl. As used herein, an "in-chain" atom refers to an atom substituted for a perfluoroalkyl carbon at a position other than the α or ω positions of the C$_{2-10}$ perfluoroalkylene group.

There is also provided a process for preparing a polyfluoro γ-ketoester compound of the foregoing formula whch comprises:

(a) contacting and forming a reaction mixture, in an aprotic solvent at a temperature between —20° C. and 100° C., of approximately equimolar quantities of an ethylenic monoolefin CF$_2$=CFY, a metal cyanide or quaternary ammonium cyanide M(CN)$_a$, and a fluoroester $R_FCO_2R$; and (b) reacting the reaction mixture formed in step (a) with a molar excess of an alcohol R$^1$OH and a molar excess of mineral acid to form the polyfluoro γ-ketoester; or (b') hydrolyzing the reaction mixture formed in step (a) by adding an aqueous solution of a mineral acid until an acid concentration of at least 0.1M is achieved, to form a mixture comprising intermediates selected from the group consisting of (1) a polyfluorinated lactam

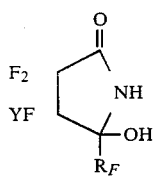

(2) a polyfluorinated ketoacid

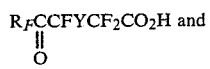

its cyclic tautomer

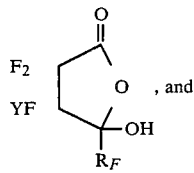

(3) both (1) and (2); and (c) reacting the mixture formed in step (b') with a molar excess of an alcohol R$^1$OH and a molar excess of mineral acid to form the polyfluoro γ-ketoester; wherein $R_F$, $R^1_F$, X, $R^1$, and Y are defined as above, R is defined as $R^1$, M is an alkali metal, or quaternary ammonium, and a is the valence of M.

In addition to process intermediates and a lactone byproduct, this invention also provides acyl fluoride, vinyl ether and allyl ether derivatives of the polyfluoro γ-ketoester of the formula:

$$R^1O_2CCF_2CFYZ,$$

wherein $R^1$ and Y are defined as above, Z is $-CF(R^1_FX)OQ_nCF(CF_3)COF$, $-CF(R^1_FX)OQ_nCF=CF_2$, or $-CF(R^1_FX)OQ_mCF_2CF=CF_2$, X is defined as above except that X may not be —F, Q is $-CF(CF_3)CF_2O-$, m is an integer from 0 to 7, and n is an integer from 0 to 6.

The invention further provides copolymers, with fluorinated monoolefinic comonomers, of the polyfluoro γ-ketoester and its vinyl ether and allyl ether derivatives.

DETAILED DESCRIPTION OF THE INVENTION

The compounds and process of the instant invention can be understood by reference to the following generalized process:

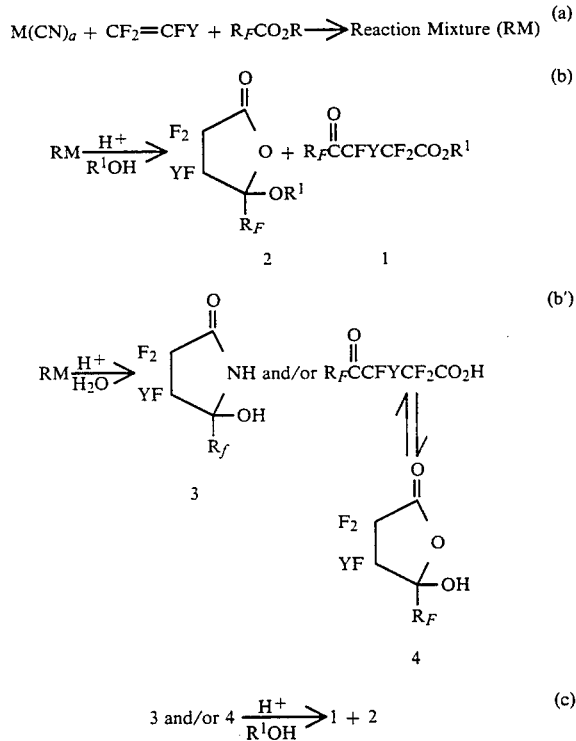

Preferred compounds of the invention are those in which, in the foregoing process, R and $R^1$ are —CH$_3$ or —CH$_2$CF$_3$; Y is —F; $R^1_F$ is —CF$_2$CF$_2$—; and X is —SR$^2$, —SO$_2$R$^2$, or —N$_3$.

In the first step of the process of the invention, a fluoroolefin, a metal or quaternary ammonium cyanide and a fluoroester are mixed under reaction conditions to form a reaction mixture. The metal cyanide can be an alkali metal cyanide or an alkaline earth metal cyanide. Suitable quaternary ammonium cyanide compounds include tetraethylammonium cyanide and tetramethylammonium cyanide. The fluoroolefin and fluoroester reactants, which can be, for example, tetrafluoroethylene and trifluoroethyl trifluoroacetate, can be prepared according to techniques known in the art. The reactants can be mixed in any order or added continuously. Relative amounts of the various reactants are not critical; however, approximately equimolar quantities are preferred. The temperature for the initial reaction is maintained in the range of about −20° C. to 100° C., and preferably maintained between about −10° C. and 75° C. In a most preferred process, the reactants are mixed at a temperature below 10° C., followed by heating to a reaction temperature if this is selected to be above 10° C. The required reaction time can very considerably, depending upon reaction temperature. Generally, the reaction time will be between several minutes to about 12 hours. Reaction pressure is not critical, but elevated reaction pressures between about 172 and 3,448 kPa (25 and 500 psi) are preferred. Aprotic solvents are required, and polar aprotic solvents are preferred. Suitable solvents for the process of the invention include dimethyl sulfoxide (DMSO), acetonitrile, tetraglyme, and dimethylformamide.

Intermediates (3) and (4) are obtained by removing volatile fractions from the reaction mixture by evaporation under reduced pressure, leaving a residue, which is then treated with aqueous mineral acid. Under mild aqueous acid conditions, for example, when reaction temperatures are maintained below 40° C. and acid concentrations are maintained in the range from about 0.1M to about 4M, a mixture of intermediates (3) and (4) is obtained. Under conditions of severe acid treatment, in which higher reaction temperatures and acid concentrations are employed, intermediate (3) is usually not present and intermediate (4) is provided in the form of a tautomeric mixture of a cyclic lactone and acyclic ketoacid. Intermediates (3) or (4) can be isolated by extraction into an appropriate solvent such as diethyl ether, followed by fractional distillation of the resulting extract. As an optional step, intermediate (4) can be distilled directly from the reaction mixture following addition of an excess of concentrated mineral acid, for example, concentrated H$_2$SO$_4$.

Polyfluoro γ-ketoester (1) and a polyfluorolactone by-product (2) are obtained by treating the original reaction mixture, or intermediate (3), or intermediate (4), or any mixture thereof, with a molar excess of alcohol R$^1$OH, R$^1$ being defined as previously given, preferably methanol or 2,2,2-trifluoroethanol, and a slight molar excess of concentrated mineral acid. A 10 to 30-fold molar excess of alcohol and a 1-3 fold molar excess of acid are suitable. In this step, a reaction temperature of between about 10° C. to about 50° C. is maintained. The products, polyfluoro γ-ketoester 1 and polyfluorolactone byproduct 2, can be recovered by distillation and further purified by fractional distillation. In a preferred process of the invention, the impure ketoester, which can be in the form of a ketone hemiketal or hydrate, is treated with P$_2$O$_5$ prior to fractionation, particularly when a substantial excess of the alcohol R$^1$OH has been used in the esterification step.

If desired, the polyfluoro γ-ketoester (1) and its lactone by-product (2) can be prepared directly from the original reaction mixture without first preparing intermediates 3 or 4. In this embodiment, the first reaction step is conducted substantially as described previously. After evaporation of volatile fractions under reduced pressure, the evaporated reaction mixture is treated with aqueous acid, then with alcohol R¹OH, in addition to sufficient concentrated acid to remove water which can be present or formed during the esterification step. To promote the yield of product ester 1, the water concentration in the evaporated reaction mixture must be minimized. Yields of product ester 1 can be improved by use of an anhydrous HCl in an alcohol, e.g., methanol, or by use of concentrated H₂SO₄ as an acid reactant.

Polyfluorolactone (2) can be converted to polyfluoro γ-ketoester (1) by additional treatment with excess alcohol and concentrated mineral acid. As described previously, the impure product (1) can be treated with P₂O₅ and subsequently recovered by fractional distillation. A similar process for converting polyfluorolactones to acyclic polyfluoroketoesters is described in U.S. Pat. No. 4,335,255.

The present invention also includes certain HFPO adduct acyl fluoride, vinyl ether and allyl ether derivatives of the polyfluoro γ-ketoester of the invention. These compounds have the formula

R¹O₂CCF₂CFYZ, where R¹ is —CH₃, —C₂H₅, —CH₂CF₃ or —CH₂(CF₂CF₂)₁₋₆H; Y is —F or —Cl; and Z is —CF(R¹$_F$X)OQ$_n$CF(CF₃)COF, —CF(R¹$_F$X)OQ$_n$CF=CF₂ or —CF(R¹$_F$X)OQ$_m$CF₂CF=CF₂, where R¹$_F$ is a C₂₋₁₀ perfluoroalkylene group optionally containing 1 to 2 in-chain ether oxygen atoms separated by at least 2 carbon atoms, X is —OR², —SR², —SO₂R², —SO₂F, —SO₂Cl, or —N₃, where R² is —CH₃, —C₂H₅ or —C₆H₅; and Q is —CF(CF₃)CF₂O—, m is an integer from 0 to 7, and n is an integer from 0 to 6.

To form the HFPO adduct acyl fluorides, the polyfluoro γ-ketoester can be reacted with hexafluoropropane oxide (HFPO), to form the acyl fluoride derivative in which Z is —CF(R¹$_F$X)OQ$_n$CF(CF₃)COF.

This derivative can be further treated to form the allyl ether derivative of the invention by reacting the adduct acyl fluoride with perfluoroallylfluorosulfate or perfluoroallyl chloride in the presence of fluoride ions, using process conditions described in U.S. Pat. Nos. 4,273,728, 4,273,729 and 4,275,225. The pertinent passages of these patents are incorporated herein by reference.

The acyl fluoride HFPO adduct of the polyfluoro γ-ketoester can be converted to the vinyl ether derivative of the invention by pyrolyzing the acyl fluoride containing at least one Q group, and preferably at least two such groups, in the presence of a carbonate, phosphate, sulfite or sulfate salt of an alkali or alkaline earth metal, preferably sodium carbonate or trisodium phosphate, all in an aprotic solvent. Suitable process conditions are described in U.S. Pat. No. 4,335,255, the appropriate passages of which are incorporated herein by reference.

To form the copolymers of the invention, the polyfluoro γ-ketoester compounds of the invention can be copolymerized directly with such comonomers as ethylene or partly fluorinated ethylenes such as vinylidene fluoride or vinyl fluoride, as set forth in the following generalized formula:

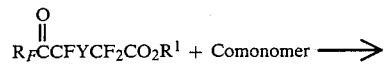 + Comonomer ⟶

-continued

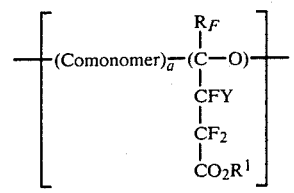

In the foregoing formula, and in the claims, "(comonomer)" refers to the saturated residue of the olefin or fluoroolefin employed in the copolymerization mixture. In the foregoing formula, R$_F$, Y, and R¹ are as previously defined, and a is an integer which is at least 2. An upper limit for the value of a is about 100. In addition, such fully-fluorinated monoolefins as tetrafluoroethylene, hexafluoropropene, or certain perfluoroalkylvinyl ethers in which the alkyl group contains between 1 and 4 carbon atoms, may be incorporated into the copolymers of the polyfluoro γ-ketoester provided that one or more of the previously mentioned hydrogen-carrying monoolefins are also present in the polymerization mixture.

The copolymers of the invention which are formed from the allyl ether and vinyl ether derivatives of the polyfluoro γ-ketoester are obtained by copolymerizing a selected derivative with one or more fluorinated monoolefins such as tetrafluoroethylene, trifluoroethylene, vinylidene fluoride, or mixtures of tetrafluoroethylene with hexafluoropropene and perfluoroalkyl vinyl ethers. Suitable processes are disclosed in U.S. Pat. Nos. 4,273,728, 4,273,729 and 4,275,225.

INDUSTRIAL UTILITY

The copolymers of the invention can be molded by processes known in the art into useful articles, such as films. Pendant functional groups X, which in certain preferred embodiments of the invention include —SO₂R², —SR², and —N₃, confer special utility to the copolymers of the invention. The pendant group —SR² can be converted to —SO₂R², —SO₂F, or —SO₂Cl by techniques such as those disclosed, for example, by Ward, *J. Org. Chem.* 30: p. 3009 (1965). These pendant groups permit the shaped polymer films of the invention to be used as ion-exchange membranes, as described in U.S. Pat. No. 4,176,215, or as electrolysis cell diaphragm materials, as disclosed in U.S. Pat. Nos. 4,164,463 and 3,853,720. The copolymers of the invention which contain pendant —N₃ groups can be converted to chemically stable, structural foams by heating to a temperature which causes the copolymer to release N₂ as a gas. The gas serves as a blowing agent.

In addition, copolymers of the invention containing pendant —N₃ groups can be further modified by reaction of pendant —CF₂N₃ groups with a tertiary phosphine such as triphenylphosphine, producing cyano-substituted copolymers. These cyano-substituted copolymers provide cure sites which permit further conversion of the copolymers to fluoroelastomers, as disclosed in U.S. Pat. No. 4,281,092.

The following examples are provided to further illustrate the present invention. In the examples, all parts and percentages given are by weight and all temperatures are in degrees Celsius.

For structure confirmation analyses, fluorine nuclear magnetic resonance chemical shifts are set forth in parts per million from internal fluorotrichloromethane. Infrared and nuclear magnetic resonance spectra were recorded on undiluted liquid samples unless otherwise stated.

EXAMPLE 1

4-Ketoheptafluoropentanamide Cyclic Lactam

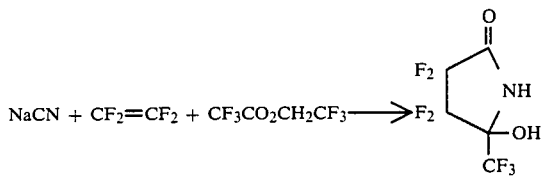

A 400-ml tube containing 24.5 g (0.50 mol) of sodium cyanide, 150 ml of dimethyl sulfoxide (DMSO), 117.6 g (0.60 mol) of trifluoroethyl trifluoroacetate, and 50 g (0.50 mol) of tetrafluoroethylene was agitated under ambient conditions for 8 hr., then at 50° for 4 hr. The resulting dark reaction mixture was poured into a solution of 200 ml of concentrated $H_2SO_4$ in 1000 ml of water, and the resulting mixture stirred at 25° for one week. Continuous extraction with ether and fractionation of the resulting extracts provided a partially solid fraction, boiling point (bp) 45°–100° (1 mm), 28.6 g. Distillation of volatiles up to bp 84° (7 mm) left 20.5 g (17%) of impure 4-ketoheptafluoropentanamide cyclic lactam as a deliquescent solid. An analytical sample was obtained by pressing the solid dry in a dry box, mp 82°–87°, IR (nujol): 2600, 2830, 2930 (broad, OH—NH), 1760 (C=O), and 1300–1100 cm$^{-1}$ (CF, C—O). NMR (CD$_3$CN): $^1$H 8.78 (broad s, 1H) and 6.44 ppm (broad s, 1H) for OH+NH; $^{19}$F-79.3 ppm (d of q, $J_{FF}$ 15.7, 2.4 Hz, 3F, CF$_3$) with an AB for one ring CF$_2$ at −11524, −11808, −11859, and −12141 Hz (m, 2F) and an AB for the other ring CF$_2$ at −11715 and −11969 Hz (m, 1F) and −12330 and −12586 Hz (q of t, $J_{FF}$ 15.7, 4.6 Hz, 1F). Mass spec. (E.I.): m/e 172 (M$^+$—CF$_3$, 128 (C$_2$F$_4$CO$^+$), 109 (C$_2$F$_3$CO$^+$), 100 (C$_2$F$_4^+$), 96 (CF$_3$C=NH$^+$), 69 (CF$_3^+$), 44 (H$_2$NCO$^+$).

Anal Calcd. for $C_5H_2F_7NO_2$: C, 24.91; H, 0.84; N 5.81. Found: C, 25.09; H, 1.00; N, 5.88

EXAMPLE 2

Methyl 4-Ketoheptafluoropentanoate

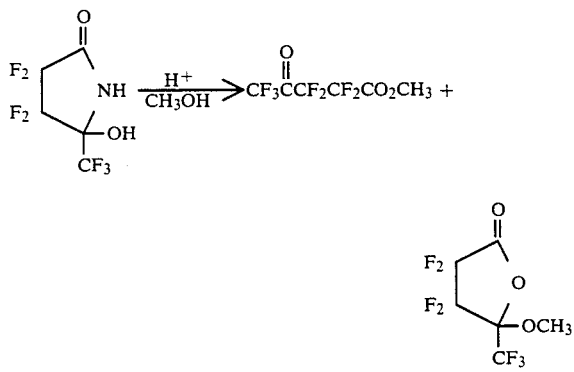

An impure sample of 4-ketoheptafluoropentanamide cyclic lactam, prepared by a process substantially similar to that described in Example 1, (28.1 g, 0.12 mol), was combined with 64.0 g (2.0 mol) of methanol and 7 ml (14 g, 0.14 mol) of concentrated $H_2SO_4$. The resulting mixture was allowed to stand for 12 days at 25°. Distillation provided 35.6 of higher boiling fractions [bp ca 20°—48°, 0.5 mm], which were treated with 30 g (0.21 mol) of $P_2O_5$ and then redistilled. There was thus obtained 12.0 g (39%) of methyl 4-ketoheptafluoropentanoate, bp 104°. IR (CCl$_4$): 3010, 2960, and 2850 (sat'd CH), 1790 (keto C=O), 1760 (ester C=O), and 1250–1150 cm$^{-1}$ (CF, C—O) with a weak band at 1855 cm$^{-1}$ for isomeric lactone impurity. NMR (CCl$_4$): $^1$H 3.98 ppm (s, CH$_3$O) with a band at 3.76 ppm for 7% of isomeric lactone; $^{19}$F-75.5 (t of t, $J_{FF}$ 8.3, 2.9 Hz, 3F, CF$_3$), −119.6 (t of g, $J_{FF}$ 4.1, 2.9 Hz, 2F, CF$_2$), and −121.5 ppm (g of t, $J_{FF}$ 8.3, 4.1 Hz, 2F, CF$_2$). Analysis by GC indicated the presence of 8% of a minor component. Both components were characterized by GC/MS. For the major component, C.I. m/e 257 (M+H$^+$) indicated the proper 256 molecular weight; E.I. m/e 197, (CF$_3$COCF$_2$CF$_2^+$), 187 (CH$_3$O$_2$CCF$_2$CF$_2$CO$^+$), 159 (CH$_3$O$_2$CCF$_2$CF$_2^+$), 109 (CH$_3$O$_2$CF$_2^+$), 97 (CF$_3$CO$^+$), 69 (CF$_3^+$), 59 (CH$_3$O$_2$C$^+$). For the minor cyclic component, C.I., m/e 257 (M+H$^+$); E.I. m/e 212 (M$^+$—CO$_2$), 162 CF$_3$C(OCH$_3$)=CF$_2^+$), 100 (C$_2$F$_4^+$), 69 (CF$_3^+$).

Anal Calcd. for $C_6H_3F_7O_3$: C, 28.14; H, 1.18. Found: C, 28.16; H, 1.30.

EXAMPLE 3

2,2,2-Trifluoroethyl 4-Ketoheptafluoropentanoate

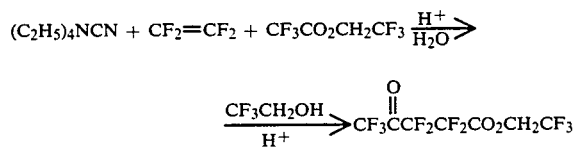

A 400-ml tube containing 62.4 g (0.40 mol) of tetraethylammonium cyanide, 150 ml of acetonitrile, 78.4 g (0.40 mol) of trifluoroethyl trifluoroacetate, and 50 g (0.50 mol) of tetrafluoroethylene was shaken at ambient temperature for 8 hr. Evaporation of volatiles from the resulting reaction mixture under reduced pressure provided a viscous residue which was treated with 400 ml of water and 200 ml of concentrated $H_2SO_4$. The mixture was stirred at 25° for 3 days, then at 70°–80° for 3 days. Continuous extraction with ether for 12 hr. and distillation of the extract to a head temperature of 66° afforded 118 g of residual crude acid, which was stirred with 100 g (1.0 mol) of trifluoroethanol and 150 ml of concentrated $H_2SO_4$ for 3 days. Distillation provided 179.4 g of liquid, bp 30° (1 mm) or below. This liquid was fractionated, removing most of the trifluoroethanol, and leaving a residue. $P_2O_5$, 15 g, was added to the residue, and fractionation was continued, giving 20.7 g (16%) of 2,2,2-trifluoroethyl 4-ketoheptafluoropentanoate, bp 61°–67° (100 mm), which contained ca 3% impurities by GC analysis. A single fraction, bp 65°–66° (100 mm), was analyzed. IR (CCl$_4$): 2990 (sat'd CH), 1800 (acyclic C=O), 1300–1100 cm$^{-1}$ (CF, C—O), with C=O of cyclic impurity also present at 1860 cm$^{-1}$. $^1$H and $^{19}$F NMR spectra fit the assigned structure, above, consistent with the presence of a small amount of impurities.

Anal Calcd. For $C_7H_{12}F_{10}O_3$: C, 25.94; H, 0.62. Found: C, 25.79; H, 0.65.

EXAMPLE 4

Equilibrium Mixture of Ring-Chain Tautomers of 4-Ketoheptafluoropentanoic Acid $$(C_2H_5)_4NCN + CF_2=CF_2 + CF_3CO_2CH_2CF_3 \xrightarrow[H_2O]{H^+}$$

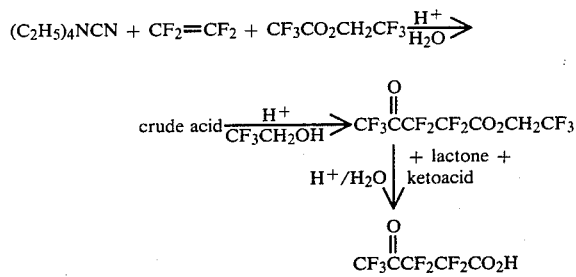

A reaction mixture, prepared in substantially similar fashion to the reaction mixture of Example 3, above, was shaken at about 50° for 8 hr. Evaporation of volatiles from the reaction mixture provided a residue which was subsequently hydrolyzed with 200 ml of concentrated $H_2SO_4$ and 400 ml of water at about 80° for 3 days. Continuous extraction of the resulting mixture with ether, followed by distillation of ether from the resulting extract, provided 125 g of crude ketoacid. Esterification was conducted by treating the crude ketoacid with 200 g (2.0 mol) of trifluoroethanol and 200 ml of concentrated $H_2SO_4$ at about 25° for 6 days. Volatiles were removed under reduced pressure and trifluoroethanol was distilled from the volatiles, leaving a residue. 50 g of $P_2O_5$ were added to this residue and fractionation was continued to afford a 24.8 g (19%) fraction, bp 64°–72° (10 mm), shown by GC analysis to be mainly $CF_3C(O)CF_2CF_2CO_2CH_2CF_3$, and 38.3 g of a mixture of the ketoester and parent acid, bp 72°–75° (100 mm).

A relatively pure fraction of 4-ketoheptafluoropentanoic acid was obtained by treating the combined fractions above with 50 ml of water and 10 ml of concentrated HCl for several days, removing trifluoroethanol and some water by distillation, and distilling the resulting hydrated acid from concentrated $H_2SO_4$. There was thus obtained 42.7 g (44% from tetrafluoroethylene) of 4-ketoheptafluoropentanoic acid as the tautomeric mixture, bp 51° (30 mm). IR ($CHCl_3$): 3500 (broad, OH), 1850 (ring C=O), 1770 (open-chain C=O), 1300–1100 $cm^{-1}$ (CF, C—O). The relative intensities of the carbonyl adsorptions indicated appreciable amounts of open-chain and cyclic tautomers, with the cyclic (lactol) form predominating. NMR ($CDCl_3$): $^1H$ and $^{19}F$ spectra were consistent with a mixture of lactol and ketoacid, with lactol a major component. GC analysis showed a single component.

Anal Calcd. for $C_5HF_7O_3$: C, 24.81; H, 0.42; F, 54.94. Found: C, 24.76; H, 0.24; F, 54.37.

EXAMPLE 5

Copolymer of Vinylidene Fluoride and 2,2,2-Trifluoroethyl-4-Ketoheptafluoropentanoate

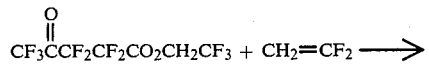

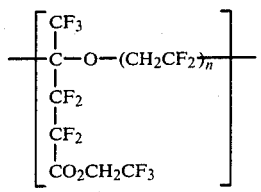

A 100-ml tube, containing 12.2 g (0.038 mol) of 2,2,2-trifluoroethyl 4-ketoheptafluoropentanoate, 25 ml of $CFCl_2CF_2Cl$, 3 ml of 3% perfluoropropionyl peroxide in $CFCl_2CF_2Cl$, and 30 g (0.47 mol) of vinylidene fluoride was shaken at about 40° for 2 hr. after an initial mild exothermic reaction. The resulting polymeric product was recovered by evaporation of volatiles under reduced pressure at 25° (0.1 mm) providing 26.2 g of a solid copolymer. An analytical sample was obtained by thorough extraction with ether and drying of the resulting residue under vacuum. IR (nujol): 1795 $cm^{-1}$; (C=O) band prominent in the spectrum.

I claim:
1. A compound of the formula

wherein
$R_F$ is $—R^1_FX$,
where
$R^1_F$ is a perfluoroalkylene group of 2–10 carbon atoms, optionally containing 1 or 2 in-chain ether oxygen atoms separated by at least 2 carbon atoms, and
X is $—SR^2$
where
$R^2$ is $—CH_3$, $—C_2H_5$ or $—C_6H_5$;
$R^1$ is $—CH_3$, $—C_2H_5$, $—CH_2CF_3$ or $—CH_2(CF_2CF_2)_{1-6}H$; and
Y is $—F$ or $—Cl$.
2. A compound according to claim 1, wherein $R^1$ is $—CH_3$ and Y is $—F$.
3. A compound according to claim 2, wherein $R^1_F$ is $—CF_2CF_2—$.
4. A compound according to claim 3 wherein $R^2$ is $—CH_3$.
5. A compound of the formula

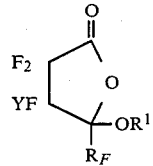

wherein
$R_F$ is $—R^1_FX$,
where
$R^1_F$ is a perfluoroalkylene group of 2–10 carbon atoms, optionally containing 1 or 2 in-chain ether oxygen atoms separated by at least 2 carbon atoms, and
X is $—SR^2$
where
$R^2$ is $—CH_3$, $—C_2H_5$ or $—C_6H_5$;
$R^1$ is $—CH_3$, $—C_2H_5$, $—CH_2CF_3$ or $—CH_2(CF_2CF_2)_{1-6}H$; and
Y is $—F$ or $—Cl$.

* * * * *